United States Patent [19]
Tada et al.

[11] Patent Number: 5,849,993
[45] Date of Patent: Dec. 15, 1998

[54] TRANSGENIC MICE AS A MODEL FOR METABOLIC BONE DISEASES

[75] Inventors: Norihiro Tada; Masahiro Sato, both of Kawagoe; Takashi Kobayashi, Fukuoka; Toru Ikeda, Narashino; Katsuiku Hirokawa, Tokyo, all of Japan

[73] Assignee: Hoechst Japan Limited, Tokyo, Japan

[21] Appl. No.: 428,316

[22] Filed: Apr. 25, 1995

[30] Foreign Application Priority Data

Apr. 27, 1994 [JP] Japan .................................. 6-110202

[51] Int. Cl.$^6$ .............................. C12N 5/00; C12N 15/00; C12N 15/09
[52] U.S. Cl. ......................... 800/2; 435/69.7; 435/69.1; 435/172.3; 435/91.2; 424/9.2; 536/23.1; 536/23.4; 536/23.5; 536/24.1
[58] Field of Search ............................... 800/2; 435/69.7, 435/69.1, 172.3, 91.2; 424/9.2; 536/23.1, 23.4, 23.5, 24.1

[56] References Cited

PUBLICATIONS

Breitman et al., Science, vol. 238(4833): 1563–1565 (1987)
Baker et al., Osteoblast–Specific Expression of Growth Hormone Stimulates Bone Growth in Transgenic Mice, Mol. & Cell. Biol. 12:5541–5547 (1992).
Kesterson et al., The Human Osteocalcin promoter Directs Bone–Specific Vitamin D–Regulatable Gene Expression in Transgenic Mice Mol. Endo. 7(3) :462–467 (1993).
Palmiter et al., Cell Lineage Ablation in Transgenic mice by Cell–Specific Expression of a Toxin Gene, Cell 50:435–443 (1987).
Behringer et al., Dwarf mice produced by genetic ablation of growth hormone–expressing cells, Genes & Develop. 2:453–461 (1988).
Stojek & Wagner, Genetic Engineering, vol. 10, pp. 221–246, 1988.
Bradley et al., Biotechnology, vol. 10, pp. 534–539, 1992.
Goldberg et al., Journal of Cellular Biochemistry, vol. 58, pp. 499–508, Aug. 1995.
Sato et al., Biochemical and biophysical Research Communications, vol. 215, pp. 412–421, Oct. 4, 1995.
Klein et al., Laboratory Investigation, vol. 67, pp. 31–41, Jul. 1992.
Lian et al., Proceedings of the National Academy of Sciences of the USA, vol. 86, pp. 1143–1147, Feb. 1989.

*Primary Examiner*—Jasemine C. Chambers
*Assistant Examiner*—Jill D. Schmuck
*Attorney, Agent, or Firm*—Finnegan, Henderson, Farabow, Garrett & Dunner, L.L.P.

[57] ABSTRACT

Transgenic mice carrying a recombinant DNA construct comprising the gene encoding diphtheria toxin A chain operably linked to a osteocalcin promoter. The transgenic mice can be used as a model for metabolic bone diseases since they have decreased bone mass associated with a marked reduction in the number of osteoblasts.

2 Claims, 6 Drawing Sheets

LANE 1 = OC - DT - A - 1803 - 3
LANE 2 = OC - DT - A - 1803 - 4
LANE 3 = OC - DT - A - 1803 - 5
LANE 4 = OC - DT - A - 1803 - 6
LANE 5 = OC - DT - A - 1803 - 7
LANE 6 = OC - DT - A - 1803 - 8
LANE 7 = OC - DT - A - 1803 - 9
LANE 8 = OC - DT - A - 1803 - 10

LANE 1 = OC - DT - A - 1803 - 3
(BONE TISSUES OF A Tg MOUSE)

LANE 2 = BONE TISSUES OF A NON-Tg MOUSE

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAATTCAAGA ACAACCTTCA CTTTAAT                      2 7

( 2 ) INFORMATION FOR SEQ ID NO:2:

( i ) SEQUENCE CHARACTERISTICS:
        ( A ) LENGTH: 27 base pairs

```
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTCGAGTTGC  TGTGTGGGAC  TTGTCTG                                               2 7
```

TRANSGENIC MICE AS A MODEL FOR METABOLIC BONE DISEASES

"This application claims priority of Japanese application Ser. No. 110202/94, filed Apr. 24, 1994."

BACKGROUND OF THE INVENTION

1. Field of the Invention

The present invention relates to a model animal which is useful in the development of medical agents generally concerning the treatment of metabolic bone diseases. More particularly, it is concerned with a transgenic animal designed to specifically express diphtheria toxin A controlled by osteocalcin promoter in osteoblasts of the bone tissues.

2. Description of the Prior Art

Nowadays, the aged society is advancing rapidly and senile osteoporosis is growing as a serious social problem. All the aged are suffering from various disorders, more or less, caused by abnormal speeds of bone resorption. The symptoms such as lumbar and dorsal curvatures, functional disorders of arthroses and being subject to fractures are all due to the same cause. Consequently, epoch-making developments of the prophylactic and therapeutic methods against the abnormal speeds of bone resorption are urgently desired. Most of the patients with osteoporosis suffer from lumbago and dorsalgia, and are as a matter of course compelled to spend a lowered quality of daily life, and fractures due to fragility of bone, in particular, the femorotibial fracture may cause the state of so-called "Bedridden Old". The number of osteoporotic patients in Japan are said to count about 4 to 5 million, and the yearly occurrence of fractures due to osteoporosis is estimated at about a hundred thousand people (Orimo, H. et al., NIHON-IJI-SHINPO, Vol. 43, p. 3420, 1989).

It is expected that recent active development for cellular- and molecular-biological studies on bones may elucidate a pathosis of osteoporosis. In line with the studies, vigorous efforts have been made to develop the diagnostic agents and therapeutic agents. It is very important for determining a physiological and pharmacological effects of those medical agents to use a model animal showing a similar pathosis to human osteoporosis. A model animal mainly used for determining the effect of medical agents for osteoporosis is currently confined to the artificially ovariectomized female rat which is designed to show a similar pathosis to human osteoporosis. However, it is extremely difficult, only with an assay by using this rat, to evaluate the effect of medical agents for the disease which embraces various pathoses and factors. Consequently, it is important to use, depending upon purposes, various different-typed model animals which have a partially similar pathosis to the objective disease, when an assay in vivo is carried out for determining the effect of medical agents for human diseases including the present one.

Osteoblasts are the most important cells for bone formation. Functional abnormality of osteoblasts brings various metabolic bone diseases.

A mechanism of bone remodeling can be roughly divided into two phases, viz., bone resorption by osteoclasts and subsequent bone formation by osteoblasts. The relation of a functional conjugation of these two different cell lineages is considered to be maintained by a precise intercellular response mechanism. Namely, a receptor of the factors which promote bone resorption by osteoclasts does not exist in osteoclasts but in osteoblasts, and the bone resorption promoting activity is largely brought on indirectly via the pathway of an activity to osteoblasts. On the other hand, these factors are involved in proliferation and functional regulation of osteoblasts by influencing the production and functional expression of bone formation promoting factors (TGF-β, BMP and the like), and growth factors (IGF-I, IGF-II, FGF and the like) derived from osteoblasts. Therefore, growth factors derived and secreted from osteoblasts play an essential role in maintaining a metabolic balance of bone. The factors include those which are accumulated in bone matrix after being secreted from osteoblasts and released from bone matrix in accordance with the bone resorption by osteoclasts (TGF-β, BMP, IGF-II, FGF and the like) and, in addition, the factors which directly functions osteoblast cells after being secreted from osteoblasts (IGF-I and the like).

Recent development of genetic engineering has made it possible to create embryos (so-called transformed embryos) into which an exogenous gene construct (DNA) is integrated by microinjection into the nuclei of 1-cell stage embryo or by infection of preimplantation embryo with retroviral vector DNA (Gordon J. et al., Proc. Natl. Acad. Sci. USA, Vol. 77, p. 7380–7384, 1980; Jaenisch R. et al., Cell, Vol. 32, p. 209–216, 1983). The resulting embryos can further be developed to full term after transfer into the oviduct/uteri of recipient foster mothers. Some of the resulting adult animals have the exogenous DNA integrated into their own genome and to express the DNA. These transformed animals are generally called transgenic animals (hereinafter called Tg) (Gordon J. and Ruddle F., Science, Vol. 214, p. 1244–1246, 1981). The integrated exogenous DNA is called transgene. The specific transgene expression can be made in each stage from a fertilized embryo to an adult stage by combining with various promoter sequences. As a result of the expression, a protein encoded by the exogenous DNA is produced. If the said protein plays an important role on the morphogenetic pathway of individuals, some phenotypic alteration may occur at a certain stage of the development. For giving a phenotypic alteration in Tgs, two approaches are possible; 1) overexpression of a target protein in a targeted tissue or a protein for an abnormal gene and 2) suppression of endogenous target gene-expression in a mRNA level and tissue deficiency by specifically lethaling the tissues expressing a target protein by anti-sense gene technology (Katsuki M. et al, Science, Vol. 241, p. 593–595, 1988; Matsumoto K. et al., Mol. Reprod. Develop., Vol. 36, p. 53–58, 1993). These are based upon an usage of tissue-specific or ubiquitous promoter and/or enhancer, both of which should be placed at the upstream the target gene. For allowing to occur a deficiency of specific tissues by expressing toxins, there are a genetic ablation method and others (Breitman M. L. et al., Science, Vol. 238, p. 1563–1565, 1987; Palmiter R. D. et al., Cell, Vol. 50, p. 435–443, 1987; Behringer R. R. et al., Genes & Development, Vol. 2, p. 453–461, 1988).

Up to date, there are many reports to show that Tgs exhibited alteration of their original phenotypes due to the expression of a transgene. These are mentioned in detail in the reviews by Palmiter R. D. and Brinster R. L. (Annu. Rev. Genet., Vol. 20, p. 465–499, 1986) and Gordon J. W. (In. Rev. of Cytobiol., Vol. 115, p.171–229, 1989). These Tgs can be utilized in the field of 1) analysis of gene expression in vivo during embryogenesis, 2) gene therapy for overcoming or ameliorating hereditary genetical tissues, etc. Transformation of fertilized eggs with transgene can be achieved by giving the exogenous transgene, and then the added transgene shall be integrated into a host genome in the pronuclei of fertilized eggs. For introduction of the exogenous DNA into mammalian embryos, there are several methods. For example, it is widely utilized that transgene is introduced via a micropipet (so-called microinjection method) into pronuclei of 1-cell stage eggs (Gordon et al., 1980).

Mammalian fertilized eggs into which DNA is injected can be developed to full term after transfer to the oviducts or uterus of pseudopregnant female recipients. The delivered living pups can be analyzed later by PCR (polymerase chain reaction) and/or Southern blot method whether or not they would have integrated transgene in their chromosomes. If the presence of the transgene is confirmed, the Tgs shall be next analyzed for gene expression in vivo, for example, by northern blot hybridization or immunohistochemical methods. In this way, it is principally possible to introduce a certain human hereditary disease-like phenotype into an animal.

Organic constituents of bone matrix comprise mainly type I collagen (about 90%) and remaining 10% of various non-collagen proteins. Transgenic mice (hereinafter called Tg mice) showing a osteogenesis imperfecta have been created by dominant negative knock-out, overexpressing abnormal type I collagen genes (Stacey A. et al., Nature, Vol. 332, p.131–136, 1988, Pereira R. et al., J. Clin. Invest., Vol. 91, p. 709–716, 1993). Furthermore, a chondrogenetic disorder associated with a retardation of bone calcification has been confirmed in the Tg mice in which abnormal type II collagen genes were introduced (Vandenberg P. et al., Proc. Natl. Acad. Sci. USA, Vol. 88, p. 7640–7644, 1991). In this sense, it is considered that formation of cartilaginous tissues is inhibited by lowered stability of collagen fibers when even a single chain out of 3 chains forming a type II collagen contains a short abnormal collagen. However, it was impossible to establish a lineage as a disease model since many of these Tg mice died immediately after birth.

By using the same technology for producing Tg mice, it has been also known to create Tg mice which have a deficiency in specific tissues or cells by integrating a strong cytotoxin diphtheria toxin A chain (hereinafter called DT-A) with a highly tissue-specific promoter and/or enhancer (This method is called genetic ablation method or toxigenics). The method can also be utilized for investigating a cell lineage whether which stem cells differentiate in which differentiation cells.

DT-A inhibits protein synthesis in cytoplasm, leading to death of cells (Pappenheimer A. M. Jr., Ann. Rev. Biochem., Vol. 46, p. 69, 1977). Since DT-A is virulent showing a sufficient cellocidal effect only with 1 molecule per cell (Yamaizumi M. et al., Cell, Vol 15, p. 245, 1978), it is possible to strictly distinguish the cells with DT-A from those without DT-A. Such DT-A controlled by cell-specific promoter is expressed in specific cells during a specific genetic period, and as a result, those cells are led to death.

The obtained Tg mice are developed to deficient in the cells or its progeny cells. For example, the Tg mice carrying a chimeric gene in which specific expression of a DT-A gene driven by the crystalline promoter in the lens are developed phacodysplasia and finally microphthalmus (Breitman M. L. et al., Science, Vol. 238, p.1563–1565, 1987). In case an elastase I promoter was used, the promoter functions pancreas-specifically, and as a result, pancreatic exocrine cells were completely lost and a pancreatic cacogenesis was also observed (Palmiter R. D. et al., Cell, Vol. 50, p. 435–443, 1987). Furthermore, growth-hormone secreting cells in anterior pituitary were mostly lost when a growth hormone promoter was used, and growth retardation was observed (Behringer R. R. et al., Genes & Development, Vol. 2, p. 453–461, 1988). It was also proved in this case that prolactin productive cells were extremely decreased. The above facts suggest that these two cell types have been derived from the same origin, and the method appears useful for analyzing a cell lineage. Incidentally, a diphtheria toxin (hereinafter called DT) is composed of an A chain which shows cytotoxicity and a B chain which transports the A chain to cells. In the genetic ablation method which introduces only A chain genes to fertlized eggs, a DT-cytotoxicity is limited to the DT-expressing cells, and does not affect on the surrounding other cells. Thus, by using this method, an analysis can be performed based on the strict distinction of the introduced gene-expressing cells from the non-expressing cells.

About 200 kinds of non-collagen proteins are known to be present in bone (Delmas P. D. et al., Calcif. Tissue Int., Vol. 36, p. 308–316, 1984). Highly contained in particular are osteocalcin (hereinafter called OC), ostonectin and sialoprotein (osteopontin, BSP) (Termine J. D. et al., J. Biol. Chem., Vol. 256, p. 10403–10408, 1981) and they are mainly secreted from osteoblasts. OC is an acidic protein of which molecular weight is approx. 6 KDa containing a gamma carboxy glutamic acid (Gla) from further carboxylation of gamma positioned carbon of glutamic acid to vitamin D dependency (Hauschka P.V. et al., Proc. Natl. Acad. Sci. USA., Vol. 72, p. 3925–3929, 1975; Price P. A. et al., Proc. Natl. Acad. Sci. USA., Vol. 73, p. 1447–1451, 1976). It was considered that OC was a specific protein in bone tissues. However, a recent analysis of Tg mice in which was introduced chloramphenicol acetyltransferase (CAT) controlled by OC promoter has elucidated that an OC expression has been slightly found in brain and bone marrow, not only in bone tissues (Kesterson R. A. et al., Mol. Endocrinol. Vol. 7, p. 462–467, 1993).

In the femur of an adult rat (8 weeks of age), an OC is observed strongly expressed in osteoblasts which are present mainly along osteogenetic surface. However, it is not observed in the chondrocytes and in the trabecular bone just under the growth plate. In addition, a strong expression of OC is observed in almost all osteoblasts on external and internal periostea in the calvaria. On the other hand, an expression of OC in bone tissues of newborn rats is extremely low in comparison with adult rats (Ikeda T. et al., J. Histochem, Cytochem., Vol. 40, p. 1079–1088, 1992). Furthermore, a nearly similar trend to the above is proved by biochemical analysis for the amount of OC in bone tissues (Otawara Y. et al., J. Nutr. Sci. Vitaminol., Vol, 29, p. 249–260, 1983).

DETAILED DESCRIPTION OF THE INVENTION

An object of the invention is to provide a more useful model animal for metabolic bone diseases. More in detail, it is to obtain, by using an developmental-engineering and a genetic engineering technologies, Tg of which osteoblast functions important for bone metabolism are specifically injured.

The Tgs according to the present invention can be not only a useful model for bone diseases associated with a deficiency, decrease or functional depression of osteoblasts, but also an influence on bone remodeling due to osteoblast deficiency, and OC-tissue specificity can be elucidated by utilizing the Tgs.

Concerning a transgene according to the invention, a rat OC promoter can be illustrated as a tissue-specifically expressing promoter, which contains a vitamin D responsive element (VDRE), and further can be illustrated a structural gene of rabbit β-globin containing a cording region of DT-A.

The Tg mice of the invention can be a useful osteoporosis model showing the decreased bone mass associated with a marked reduction in the number of osteoblasts. Therefore, the Tg mice of the invention can be used for assay of medical agents on the inhibition of the differentiation and the activity of osteoclasts. For example, a medical agent to be assayed is given to each of groups of control animals (not the Tg mice of the invention) and the Tg mice at the same time, continuously over a period of time sufficient to improve the pathosis of the mice, followed by analysis of the bone tissues. A comparison of the above mentioned parameters shall be able to give a decision on efficacy of the medical agent. Moreover, to elucidate the conjugated mechanism of bone formation and resorption by using those mice with such a bone metabolism abnormality is extremely important not only for elucidation of pathogenetic mechanism of osteoporosis but also for establishment of its fundamental therapy or prophylaxis.

The following examples are provided to illustrate the invention and are not intended to limit the invention.

EXAMPLES

Example 1
Construction of a plasmid containing a transgene (a chimeric gene in which the expression of DT-A gene is driven by the rat OC promoter) (hereinafter called pOC/DT-A-1) and preparation of the transgene fragments The transgene was prepared as set forth below. Rat OC promoter was isolated from the liver genomic DNA of a Wistar rat, which was used as a template, and carrying out amplification of DNA fragments containing the sequence by a polymerase chain reaction (hereinafter called PCR method). Briefly, two primers (27 bp) designed to insert therebetween a fragment of the EcoR I site from −1000 to +18 which is the rat OC promoter sequence containing VDRE upstream of 5' end (Yoon et al., Biochemistry, Vol. 27, p. 8521–8526, 1988) were selected on the upstream side (sense primer: OCal-1, SEQ ID No.: 1 of the Sequence Listing) and the downstream side (reverse primer: OCal-2, SEQ ID No.: 2 of the Sequence Listing designed to have Xho I site at the 5' end), which were chemically synthesized using a DNA synthesizer and PCR-amplification. The amplified DNA fragment of 1.13 kb was digested with EcoR I and Xho I, and then purified by using 0.8% agarose-electrophoresis. Then, the fragment was subjected to subcloning at the EcoR I–Xho I site of pHSG 396 (Takeshita S. et al., Gene, Vol. 61, p. 63–74, 1987) with T4 DNA ligase. Base sequence of the rat OC promoter (Yoon et al., 1988) for the correctly integrated plasmid (pOC-1) among these plasmids was confirmed by the dideoxy method. Separately, a mammalian expression vector (pBstN) was prepared by inserting a BamH I/Sal I fragment of 1.58 kb containing the second and third exon regions of rabbit β-globin gene between BamH I and Sal I multicloning sites of pBluescript SK(-) (purchased from Stratagene, U.S.A.)

Next, the pOC-1 was digested with Xho I and then end-blunted with T4 DNA polymerase. The product was extracted with phenol/chloroform followed by ethanol-precipitation to obtain DNA. The DNA thus obtained was further digested with EcoR I, and a fragment (1.13 kb) of the rat OC promoter sequence was purified on agarose-gel electrophoresis. The rat OC promoter fragment was inserted between EcoR I/Xba I sites of pBstN (with the Xba I side end-blunted).

Separately, DT-A gene (obtained from Dr. I. Maxwell/ Health Science Center, Colorado University) was inserted into EcoR I site on the third exon of rabbit β-globin in pBstN containing the rat OC promoter sequence. The construct pOC/DT-A-1 (FIG. 1) was created by inserting the 1.13 kb fragment-containing the OC promoter sequence isolated from pBsDT-A-2 after digestion with EcoR I and Xho I and subsequent Klenow treatment-into the XbaI site (Klenow-filled) of pBstN/DT-A-17.

The standard recombinant DNA technology of Maniatis T. et al. (Molecular Cloning, A. Laboratory Manual, 1982) was used for construction of these transgenes such as DNA digestion, ligation and isolation. Also, DNA sequence at the functional region between the insert and vector was confirmed by sequencing.

Example 2
Microinjection of purified OC-DT-A into mouse fertilized eggs and transfer of the eggs Experimental animals were C57BL/6N male mice and B6C3F1 female mice (C57BL/6N×C3H/HeN) for collection of fertilized eggs and ICR female mice as a recipient for transfer of the fertilized eggs after microinjection of the DNA. First, in order to induce superovaluation, to the B6C3F1 female mice were intraperitoneally administered pregnant mare serum gonadotropin (PMSG) and human chorionic gonadotropin (hCG) each at a dose of 5 IU at an interval of 48 hours. The female mice were housed together with the C57BL/6N male mice in the same cage immediately after the administration of hCG. Next day, those B6C3F1 female mice with which a vaginal plug is recognized were defined as mated. The mated mice were promptly sacrificed, and fertilized eggs surrounded by granulosa and cumulus cells (pronucleus stage eggs) were recovered from the oviducts. The recovered fertilized eggs were transferred into M16 medium (Whittingham D. G., J. Reprod. Fert., Suppl. Vol. 14, p. 7–21, 1971) containing 1% hyaluronidase, and incubated at 37° C. in an atmosphere of 5% $CO_2$ in air, for a certain time prior to DNA injection, after removal of the granulosa and cumulus cells. The cultivation was carried out in a suspension culture dish with 35 mm diameter (No. 171099, Nunc), wherein the fertilized eggs were kept suspended in a drop (50 μl) of M16 medium covered with paraffin oil (white light mineral oil, Fisher) on the top.

The transgene was extracted after cloning the plasmid pOC/DT-A-1 prepared as above into the host E. coli and subsequent cultivation. For further purification of the plasmid, the extracts were ultra-centrifugated in cesium chloride and dialyzed after removal of ethidium bromide.

The target transgene (OC-DT-A, ca. 3.33 kb) was isolated after digestion of these purified plasmid with Sal I, Not I and Sca I and subsequent electrophoresis in a 0.8% agarose gel.

The transgene was diluted with a phosphate buffered saline (pH 7.2) immediately prior to the microinjection of the transgene. The transgene was injected into the fertilized eggs, in accordance with the operation as reported (Hogan B. et al., In Manipulating the Mouse Embryo., Cold Spring Harbor Laboratory Press, 1986). Thus, the eggs were fixed in a holding glass pipette in the medium covered with paraffin oil and then each ca. 2 pl (approx. 2,000 copies) of the DNA solution was injected into the male pronuclei of the egg using an injection glass pipette.

After the injection, the surviving eggs were transferred to the oviducts of pseudopregnant ICR recipient of Day 1 pregnancy. The recipients after the oviduct-transfer was fed until full term of gestation. A part of the fertilized eggs for the DNA injection were cryopreserved ones. The cryopreservation was carried out as reported by Tada et al. (Tada N. et al., Theriogenology, Vol. 40, p. 333–344, 1993; Tada N. et al., J. Reprod. Dev., Vol. 39, p. 139–144, 1993). Briefly, the fertilized eggs were rapidly frozen directly by plunging a cryotube (No. 366656, Nunc) containing the eggs in 30 μl of a vitrification solution (DPS: 2.75M dimethylsulfoxide: DMSO+2.75M propylene glycol+1.0M sucrose in PBI) into liquid nitrogen. Thawing was carried out by immersing the cryotube in 40° C. water bath. The thawed eggs were treated with a 0.3M sucrose solution and then washed with a PBI medium (Whittingham DG., Nature, Vol. 233, p. 125–126, 1971). The frozen-thawed eggs were cultivated until injection of the DNA.

The neonates thus produced were weaned in 4 weeks of age after birth, subjected to their tail cut at ca. 1 cm from the tip and punched on an ear for identification under anesthesia. From the tissues of the tail, DNA was extracted, which was purified and then confirmed by the Southern blot hybridization of the presence of the transgene on the chromosome of the mice. Thus, the DNA (10 μg) digested with EcoR I and BamH I was separated by electrophoresis through 0.8% agarose-gel and transferred to a nylon filter (GeneScreen Plus®, NEN, U.S.A.). The filter was dried by wind and employed to hybridization. The hybridization was carried out by a conventional method (Maniatis T. et al., 1982) in which a DT-A gene fragment was used as a probe to confirm integration of the transgene fragment into the mouse chromosome.

The results are shown in Table 1 below. In a total of 7 experiments, 541 fertilized eggs were subjected to the gene injection, of which 355 eggs (65.6%) survived after the injection. All of the survived eggs were transferred to 18 recipients, of which 10 animals became pregnant. On Day 19 of pregnancy, the pregnant recipients were subjected to cesarean section to remove 29 (8.2%) newborns. The newborns were nursed by a prepared foster mother (ICR female mouse) which had delivered on the same day. In 10 (1.8%) out of the newborns, the transgene was confirmed in the chromosome DNA extracted from the placenta. However, 3 out of the 10 were eaten by the foster mother just after nursing and could not been analyzed.

TABLE 1

Production of model mice for bone diseases by genetic engineering

Number of experiment: 7
Number of eggs injected: A 541
Number of eggs transplanted: B 355
(Percent success: B/A 65.6%)
Number of neonates survived: C 29
(Percent survival: C/B 8.2%)
Number of mice with the transgene: D 10
(Percent gene transduction: D/A 1.8%)

In one (OC-DT-A-904) out of the Tg mice not eaten by the foster mother and survived growth retardation was observed on the 7th day of birth, and in another one (OC-DT-A-603) growth retardation and symptosis were observed on the 18th day of birth. The other five Tg mice (OC-DT-A-902, -1001, -1002, -1802, -1803) grew normally and were weaned. F1 mice were further produced from each of the 5 Tg mice of which growth retardation was observed in OC-DT-A-1803 F1 Tg mice. Results of the PCR-Southern blot analysis on the DNA in the tail tissues are shown in FIG. 2. Analysis given below is mainly of the F1 mice obtained from OC-DT-A-1803 F0 mice. In the Tg mice was observed a band at ca. 170 bp which is indicative of transgene-derived mRNA.

Example 3
Transgene-derived mRNA expression

The transgene-derived mRNA expression was confirmed in OC-DT-A-1803 F1 mice by the northern blot hybridization and the RT-PCR method. The total RNA was isolated from the femurs of both the Tg F1 mice and the non-Tg F1 mice. For the northern blot hybridization, the isolated RNA 20 μg was electrophoresed in 1.1 % agarose/1.1M formaldehyde gel and then blotted onto a nylon membrane filter. Prehybridization was carried out for 2 hours at 42° C. in a hybridization buffer [containing 5×SSC (1×SSC=0.15M NaCl, 15 mM Na-citrate, pH 7.4), 50% formamide, 5 mM EDTA, 5 mg/ml heat-denatured salmon DNA, 5×Denhardt reagent, etc.]. Then, the cDNA probe (DT-A fragments) was heat-denatured by random prime labelling method and added to the hybridization buffer. Hybridization was performed for 18 hours at 42° C., and the filters were washed for 20 minutes at 56° C. in a solution containing 0.1×SSC/ 0.1% SDS. The filters were exposed to Kodak XAR-5 film with an intensifying screen for 24–72 hours at –80° C. No DT-A mRNA was detected in the femurs of the F1 mice (OC-DT-A-1803-3) so far as this method is employed, suggesting quite small amount of the transgene-derived mRNA. However, when 1 μg of the total RNA was examined using the highly sensitive RT-PCR technique (Innis, MA. et al., PCR Protocols: "A Guide to Method and Applications", Academic Press, San Diego), a band was observed at 174-bp in the femur of the OC-DT-A-1803-3 animal which is indicative of the transgene-derived mRNA. However, non-Tg mice had no transgene-derived mRNA (FIG. 3). This indicates that DT-A is expressed in Tg mice though in a very small amount.

Example 4
Changes of the total body weight in the first generation offsprings (F1) of the Tg mouse
(OC-DT-A-1803)

Body weight was measured in the offsprings (F1) born from a mated Tg mouse (OC-DT-A-1803) with a normal C57BL/6N male mice, at one week interval from the first day of birth to week 9. Whereas there was observed no difference at all between the body weight of Tg F1 mouse (OC-DT-A-1803-29) and that of a non-Tg mouse (F1) during the period immediately after birth, the difference became gradually bigger after the first week of birth. There was observed a remarkable difference in the body weight between the Tg mouse and the non-Tg mouse in the third weeks of birth. As the weeks of age progressed, growth retardation as well as abnormal behaviors were observed in Tg mouse of more than 3 weeks of age. Thus, the Tg mouse exhibited reduction of spontaneous movements and longer continued resting as well as abnormal walking around and after 4 weeks of age. Eating behavior was also insufficient to lead to death, if in a normal breeding, in almost all of the Tg animals around 4 weeks of age. It is, therefore, important in breeding such mouse to place sticky feed on the floor mat so that the animals could eat by minimum walking.

Example 5
Gene transmission to the first generation offsprings
(F1) of the Tg mouse (OC-DT-A-1803)

Out of 67 F1 animals produced by the mating as described above the number of the Tg mice was 9. This suggests that the Tg mouse is a chimera. The Tg founder mouse usually has a transgene in hemizygote in all of the cells, and a half number of the germ cells (oogonia and spermatogonia) have the transgene after meiosis. Consequently, a half number of F1 produced by mating between normal mice shall theoretically be Tg mice. In the mice in question, the reason for the production of a very low portion of Tg mice in F1 is considered that a very low portion of the F1 has the transgene in the germ cells (eggs in this case) (Table 2).

TABLE 2

Gene transmission to the first generation offspring
(F1) of the Tg mouse (OC-DT-A-1803)

| | |
|---|---|
| Number of delivery | 8 |
| Total number of newbones delivered | 67 |
| Number of newbones delivered having the transgene | 9 |

Example 6

Histological analysis of bone tissues of the Tg mice

The analysis was carried out using Tg founder mice (OC-DT-A-904) and F1 Tg mice (OC-DT-A-1803-3) obtained from OC-DT-A-1803 founder mice.

The animals were sacrificed under deep anesthesia with pentobarbital sodium, and the calvaria, femur, vertebra and mandibula were excised. These bone tissues were fixed with a solution containing 10% formalin in phosphate-buffered saline (PBS) and then decalcified by immersing in a 14% EDTA for about a week. Subsequently, these bone tissues were embedded in paraffin and sectioned to prepare continuous sliced specimens of ca. 2 μm. The specimens were subjected to hematoxylin-eosin staining and then observed under optical microscope.

A histological picture in the calvaria of a Tg founder mouse (OC-DT-A-904) is shown in FIG. 4. The trabecula of the calvaria (FIG. 4(A)) of OC-DT-A-904 was much thinner and less in the number of osteoblasts than that of a non-Tg mouse (FIG. 4(B)). Growth of the cartilage plate (growth plate) at the epiphysis of the epiphysial cartilage in the femur was much worse in the Tg founder mouse (OC-DT-A-904) than in the non-Tg mouse. The diaphysial cortex was irregularly thickened, and the femur was thin on the whole as compared with the non-Tg mouse.

FIG. 5 shows the histological picture in the vertebra of a F1 mouse (OC-DT-A-1803-3) obtained from a Tg founder mouse (OC-DT-A-1803). The trabecular bone mass of the vertebra of the F1 mouse (FIG. 4(A)) was much reduced as compared with that of the non-Tg mouse (FIG. 5(B)), and almost no osteoblasts were observed. The number of chondrocytes in the cartilage plate (growth plate) was also reduced to some extent, and the layer was also thin.

No osteoblast was observed in the histological picture in the mandibula of OC-DT-A-1803-3. There was no difference in the odontoblastic layer in the fang between Tg and non-Tg mice. It appeared normal.

A whole body photograph of a Tg mouse is shown in FIG. 6. FIG. 6 is a photograph of the whole bodies of OC-DT-A-1803-3 F1 Tg mouse (right end of the photograph) and non-Tg mice (two animals from the left). The Tg mouse was much smaller and less than a half in body weight than the other two non-Tg mice. All articles cited herein are expressly incorporated herein by reference.

---

Figure 1:
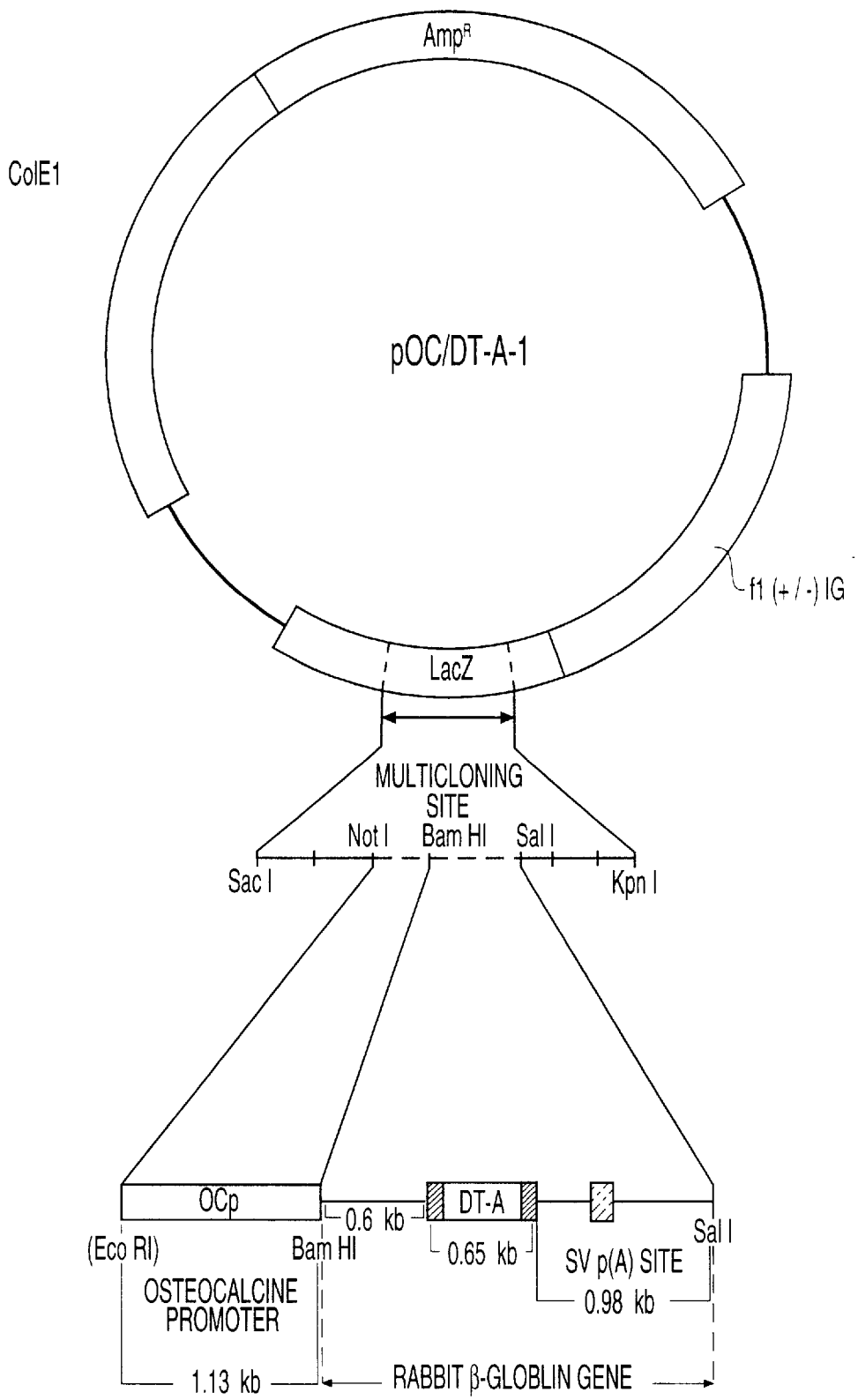
FIG. 1 shows an outline of the construction of a plasmid (pOC/DT-A-1) containing a transgene.
Figure 2:
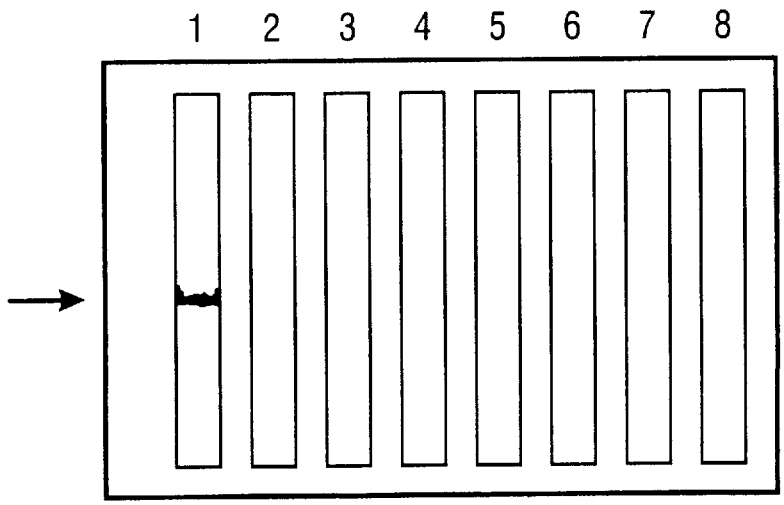
FIG. 2 shows results of a PCR-Southern blot analysis of the tail tissues from F1 mice (OC-DT-A-1803-3 to 10). The expected band (arrowed) is observed only with OC-DT-A-1803 on lane 1, which is a Tg mouse having the transgene. Other animals OC-DT-A-1803-4 to 10 (lanes 2 to 8) are non-Tg mice.
Figure 3:
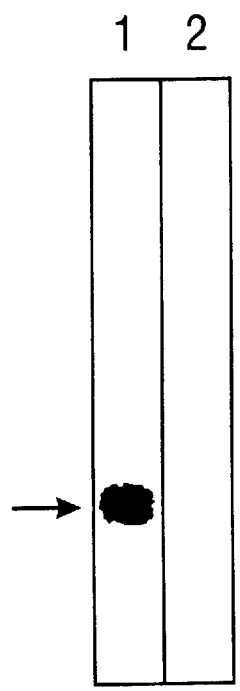
FIG. 3 shows results of the analysis by the RT-PCR technique of the entire RNA in bone tissues from a Tg mouse (OC-DT-A-1803-3) and a non-Tg mouse. Lane 1 only has the expected band (arrowed) for the Tg mouse in which mRNA originated from a transgene is expressed. Lane 2 is for the non-Tg mouse.
Figure 4A:
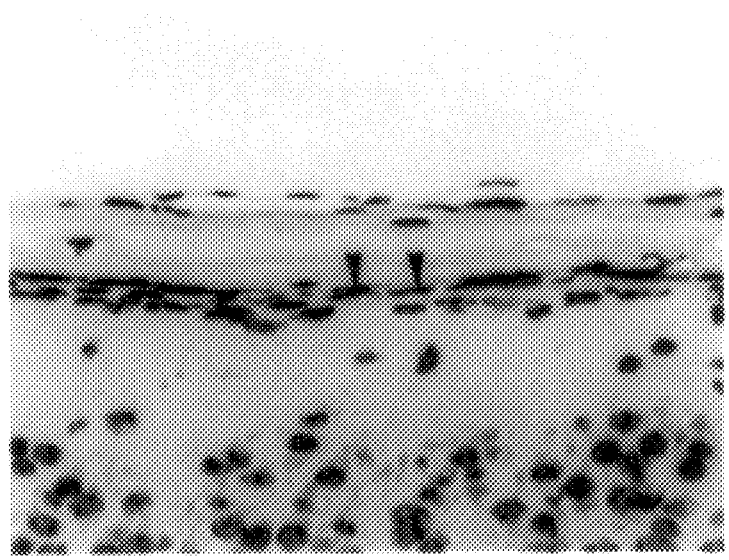
FIG. 4A–B is a photograph of the histological pictures in the calvaria of a Tg mouse (FIG. 4(A)) and a non-Tg mouse (OC-DT-A-904 FO) (FIG. 4(B)).
Figure 4B:
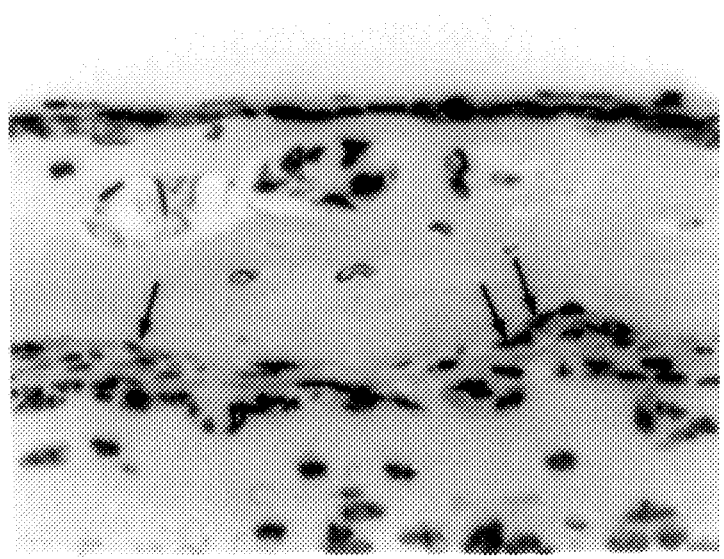
Figure 5A:
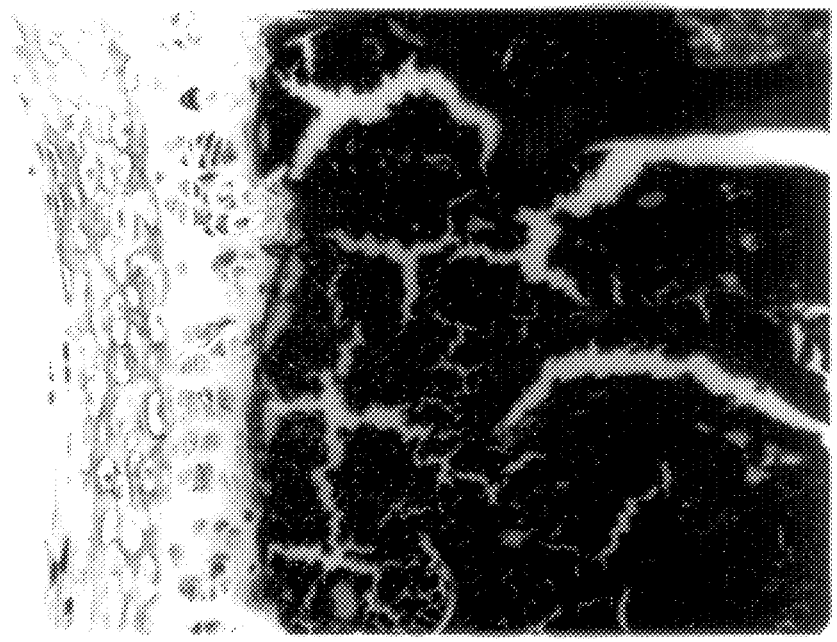
FIG. 5A–B is a photograph of the histological pictures in the vertebra of a Tg mouse (FIG. 5(A)) and a non-Tg mouse (OC-DT-A-1803-3) (FIG. 5(B)).
Figure 5B:
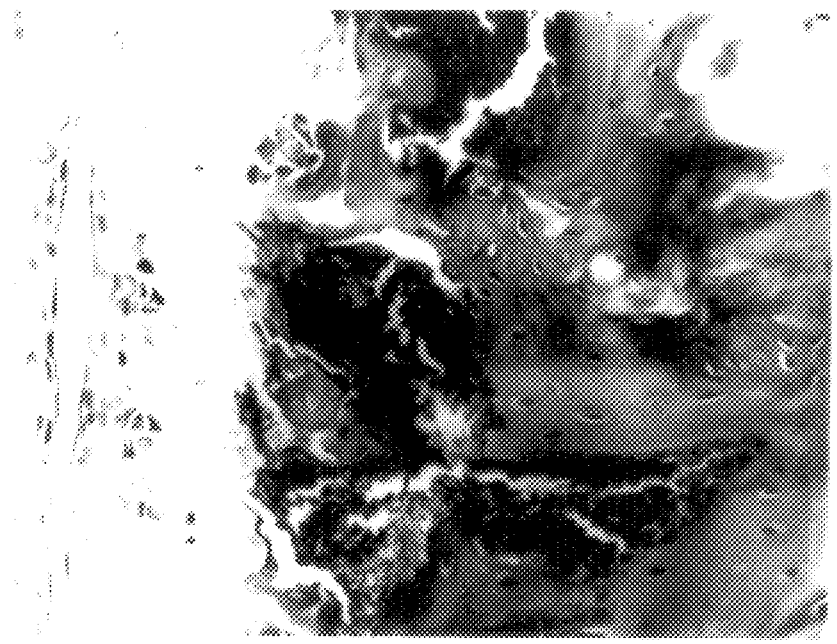
Figure 6:
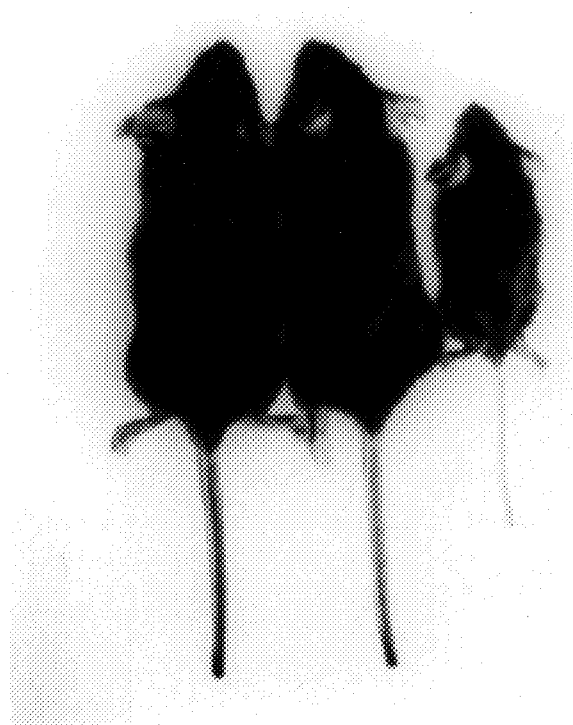
FIG. 6 is a whole body photographs of a Tg mouse and non-Tg mice (OC-DT-A-1803-3 F1).

What is claimed is:

1. A transgenic mouse displaying phenotypic characteristics indicative of metabolic bone disease, wherein said mouse lacks functional osteoblasts, wherein the genome of said mouse comprises a recombinant DNA construct consisting of the gene encoding diphtheria toxin A chain operably linked to a rat osteocalcin promoter, and wherein expression of said diphtheria toxin A chain in the osteoblasts of said mouse results in the genetic ablation of said osteoblasts in said mouse.

2. The transgenic mouse according to claim 1 characterized by a decrease in bone mass of the trabecula and bone cortex as well as by a reduction of the number of chondrocytes of the bone tissues of said mouse as a result of the expression of diphtheria toxin A chain in the osteoblasts of said mouse causing the genetic ablation of said osteoblasts in said mouse.

* * * * *